US010852236B2

(12) United States Patent
Frangioni (10) Patent No.: US 10,852,236 B2
(45) Date of Patent: Dec. 1, 2020

(54) METHOD OF MEASURING PLANT NUTRIENT TRANSPORT USING NEAR-INFRARED IMAGING

(71) Applicant: Curadel, LLC, Marlborough, MA (US)

(72) Inventor: John V. Frangioni, Wayland, MA (US)

(73) Assignee: Curadel, LLC, Natick, MA (US)

( * ) Notice: Subject to any disclaimer, the term of this patent is extended or adjusted under 35 U.S.C. 154(b) by 0 days.

(21) Appl. No.: 16/127,476

(22) Filed: Sep. 11, 2018

(65) Prior Publication Data

US 2019/0079011 A1     Mar. 14, 2019

Related U.S. Application Data

(60) Provisional application No. 62/557,432, filed on Sep. 12, 2017.

(51) Int. Cl.
*G01N 21/64* (2006.01)
*G01N 33/00* (2006.01)
*G01N 21/84* (2006.01)

(52) U.S. Cl.
CPC ..... *G01N 21/6456* (2013.01); *G01N 21/6428* (2013.01); *G01N 33/0098* (2013.01); *G01N 2021/6419* (2013.01); *G01N 2021/6421* (2013.01); *G01N 2021/6439* (2013.01); *G01N 2021/8466* (2013.01); *G01N 2201/061* (2013.01)

(58) Field of Classification Search
CPC ..... G01N 2201/061; G01N 2021/6419; G01N 2021/6421; G01N 2021/6439; G01N 2021/8466; G01N 21/6428; G01N 21/6456

USPC ......... 250/338.1, 339.05, 341.1, 342, 458.1, 250/459.1
See application file for complete search history.

(56) References Cited

U.S. PATENT DOCUMENTS

| 5,211,336 | A | * | 5/1993 | Kaidonis | A62C 3/0292 169/43 |
| 6,463,167 | B1 | | 10/2002 | Feldman et al. | |
| 6,869,593 | B2 | * | 3/2005 | Frangioni | A61K 49/0032 424/9.6 |
| 6,985,224 | B2 | * | 1/2006 | Hart | G01J 3/02 250/459.1 |
| 7,394,053 | B2 | * | 7/2008 | Frangioni | A61B 5/0059 250/208.1 |
| 7,435,876 | B2 | * | 10/2008 | Jalink | B07C 5/342 800/295 |

(Continued)

FOREIGN PATENT DOCUMENTS

| WO | WO-2016069788 A1 | 5/2016 |
| WO | WO-2016146469 A1 | 9/2016 |
| WO | WO-2016154116 A1 | 9/2016 |

*Primary Examiner* — Allen C. Ho
(74) *Attorney, Agent, or Firm* — Myers Bigel, P.A.

(57) ABSTRACT

An imaging system illuminates a portion of a plant with a light source comprising a near-infrared (NIR) light source to cause fluorescent emission by a fluorescent imaging agent absorbed by the plant and distributed within the plant via transpiration. The imaging system receives the fluorescent emission from the illuminated portion of the plant. The imaging system generates a fluorescent image of the portion of the plant from the received fluorescent emission. The imaging system displays, on a display device of the imaging system, the fluorescent image. Based on the fluorescent image, a determination that the plant has a disease or injury can be made.

23 Claims, 5 Drawing Sheets

(56) References Cited

U.S. PATENT DOCUMENTS

| | | | |
|---|---|---|---|
| 7,794,394 B2* | 9/2010 | Frangioni | A61B 5/0059 250/226 |
| 7,949,181 B2 | 5/2011 | Padfield et al. | |
| 8,107,698 B2 | 1/2012 | Kitamura | |
| 8,144,993 B2 | 3/2012 | Nishimura et al. | |
| 8,224,425 B2 | 7/2012 | Freeman et al. | |
| 8,229,548 B2* | 7/2012 | Frangioni | A61B 1/00186 600/473 |
| 8,442,289 B2 | 5/2013 | Kadomura et al. | |
| 8,472,682 B2 | 6/2013 | Guissin et al. | |
| 8,473,035 B2* | 6/2013 | Frangioni | A61B 5/415 600/476 |
| 8,492,734 B2* | 7/2013 | Yared | A61B 5/0073 250/458.1 |
| 8,620,410 B2* | 12/2013 | Frangioni | A61B 1/0005 600/473 |
| 9,326,666 B2 | 5/2016 | Frangioni | |
| 9,407,838 B2* | 8/2016 | Butte | H04N 5/332 |
| 9,710,908 B2* | 7/2017 | Yu | G01N 33/576 |
| 9,715,727 B2* | 7/2017 | Mihalca | H04N 1/6008 |
| 9,788,906 B2* | 10/2017 | Piron | A61B 6/5247 |
| 10,264,974 B2* | 4/2019 | Hong | G01N 21/6428 |
| 10,383,957 B2* | 8/2019 | de Haas | A61K 49/0091 |
| 10,467,748 B2* | 11/2019 | Kerr | G06K 9/6267 |
| 10,473,592 B2* | 11/2019 | Kramer | G01N 21/6486 |
| 10,580,130 B2* | 3/2020 | Frangioni | G06T 7/90 |
| 10,694,117 B2* | 6/2020 | Frangioni | A61B 1/043 |
| 2008/0253968 A1* | 10/2008 | Oba | G01N 21/6428 424/9.6 |
| 2010/0130871 A1 | 5/2010 | Frykman et al. | |
| 2013/0338479 A1 | 12/2013 | Pogue et al. | |
| 2015/0062153 A1 | 3/2015 | Mihalca et al. | |
| 2015/0150460 A1 | 6/2015 | Krishnaswamy et al. | |
| 2015/0339816 A1 | 11/2015 | Yu et al. | |
| 2016/0015471 A1 | 1/2016 | Piron et al. | |
| 2016/0206202 A1 | 7/2016 | Frangioni | |

\* cited by examiner

METHOD OF MEASURING PLANT NUTRIENT TRANSPORT USING NEAR-INFRARED IMAGING

RELATED APPLICATION

This application claims priority to U.S. Provisional Patent Application No. 62/557,432, filed on Sep. 12, 2017, entitled "METHOD OF MEASURING PLANT NUTRIENT TRANSPORT USING NEAR-INFRARED IMAGING" by John V. Frangioni, the contents of which are incorporated by reference herein.

TECHNICAL FIELD

The present disclosure relates generally to techniques for fluorescent imaging of a portion of a plant that has absorbed a fluorescent imaging agent.

BACKGROUND

The flow of nutrients in a plant is critical to its survival. In general, water or other nutrients (including chemicals/fertilizers supplied to the plant) travel from the roots upward through the plant body (anterograde flow) within a network of tubes called xylem. Flow downward from the leaves (retrograde flow) through this system is also important, particularly for sap collection during maple sugaring. Water, through a combination of tension, adhesion to the xylem walls, and cohesion to itself, rises through the plant where it evaporates through stomata in the leaves (or any other part of the plant exposed to air). This process, called transpiration, further aids transport of the nutrients from the roots by creating a negative pressure within the system and causing the water to be sucked up the xylem as a constant flow. Certain species of plants can absorb water and other nutrients through leaves.

Constrictions may occur in the plant xylem due to disease or injury, causing reduced nutrient flow. For example, a partial blockage or obstruction of one or more of the paths up through the plant, such as from physical damage to the plant itself or from various plant diseases or parasites, can significantly reduce flow and compromise the health of the plant.

Methods of determining and monitoring nutrient flow in a plant are known. However, these techniques often involve invasive procedures that sacrifice portions of the plant for analysis. Determination of plant health by monitoring nutrient transport in real time and on site is difficult. Furthermore, while various types of imaging systems are used in the healthcare and research fields, these have not been found readily applicable to efficiently or effectively assess and monitor the health of plants.

BRIEF DESCRIPTION OF THE DRAWINGS

The embodiments herein may be better understood by referring to the following description in conjunction with the accompanying drawings in which like reference numerals indicate identically or functionally similar elements, of which.

In the figures, reference numbers refer to the same or equivalent parts of the present invention throughout the several figures of the drawing.

SUMMARY OF THE INVENTION

According to one or more embodiments of the present disclosure, a method of imaging a portion of a plant is described. An imaging system illuminates a portion of a plant with a light source comprising a near-infrared (NIR) light source to cause fluorescent emission by a fluorescent imaging agent absorbed by the plant and distributed within the plant via transpiration. The imaging system receives the fluorescent emission from the illuminated portion of the plant. The imaging system generates a fluorescent image of the portion of the plant from the received fluorescent emission. The imaging system displays, on a display device of the imaging system, the fluorescent image. Based on the fluorescent image, a determination that the plant has a disease or injury can be made.

DETAILED DESCRIPTION

To provide an overall understanding of the invention, certain illustrative embodiments will now be described, including a method for using an imaging system to determine that a plant has a disease or injury based on a fluorescent image. Further, the imaging system, in some embodiments, may be used for generating superimposed visible and NIR images using a fluorescent imaging agent. Additionally, the fluorescent image may be used for determining a nutrient flow in the plant. However, it will be understood that the methods and systems described herein can be suitably adapted to other plant imaging applications where visible light images may be usefully displayed with diagnostic image information obtained from outside the visible light range and superimposed onto the visible light image. More generally, the methods and systems described herein may be adapted to any imaging methods in which a visible light image may be usefully displayed with a superimposed image captured from areas within the visible light image that are functionally marked to emit photons outside the visible light range by a dye or other material. These and other applications of the method described herein are intended to fall within the scope of the invention.

In the method of the present invention, a fluorescent imaging agent is absorbed by the plant and distributed by within the plant by, for example, transpiration, to portions of the plant such as a leaf, a stem, or a branch. One of such portions can be illuminated by a light source. The fluorescent imaging agent may be introduced directly into the plant, such as by injection, or may be provided onto the plant surface, such as by spraying or by directly applying the agent or an agent-containing dispersion or solution onto the portion of the plant of interest. Furthermore, the fluorescent imaging agent may be provided in a nutrient solution to be absorbed by the plant, such as through the roots or other areas exposed to the agent-containing nutrient solution. Thus, in some embodiments, the fluorescent imaging agent may be soluble in the plant nutrient, which may be water.

Furthermore, the fluorescent imaging agent may be delivered in a discrete dose, or may be continuously or intermittently applied and re-applied.

A variety of different types of fluorescent imaging agents may be introduced into the plant. In general, the fluorescent imaging agent has a specified peak absorption wavelength (also referred to herein as the excitation wavelength) and peak emission wavelength that may be used to select suitable optical hardware for use therewith. In particular, the fluorescent imaging agent may be any dye suitable for use in a plant system and having excitation and emission wavelengths suitable for components of an imaging system capable of determining a visible light image and a NIR light image, described in more detail below. For example, the fluorescent imaging agent may be at least one indocyanine green dye, fluorescein dye, methylene blue dye, and IRDye78-CA (which is the carboxylic acid form of IRDye78). As a specific example, the fluorescent imaging agent may be a dye having the structure:

wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl;

$R_3$ represents, independently for each occurrence, one or more substituents to the ring to which it is attached;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl.

As used herein, the term "acyl" refers to a group suitable for acylating a nitrogen atom to form an amide or carbamate, a carbon atom to form a ketone, a sulfur atom to form a thioester, or an oxygen atom to form an ester group, for example, a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The terms "amine" and "amino" are art-recognized and refer to both unsubstituted and substituted amines as well as ammonium salts, for example, as can be represented by the general formula:

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, for example, $R_9$, $R_{10}$, and $R'_{10}$ are selected from hydrogen, alkyl, heteroalkyl, aryl, heteroaryl, carbocyclic aliphatic, and heterocyclic aliphatic. The term "alkylamine" as used herein means an amine group, as defined above, having at least one substituted or unsubstituted alkyl attached thereto. Amino groups that are positively charged (e.g., $R'_{10}$ is present) are referred to as "ammonium" groups. In amino groups other than ammonium groups, the amine is preferably basic, for example, its conjugate acid has a pKa above 7.

The terms "amido" and "amide" are art-recognized as an amino-substituted carbonyl, such as a moiety that can be represented by the general formula:

wherein $R_9$ and $R_{10}$ are as defined above. In certain embodiments, the amide will include imides.

The term "alkyl" refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms "alkenyl" and "alkynyl" refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms "alkoxyl" and "alkoxy" as used herein refer to an —O-alkyl group. Representative alkoxyl groups include methoxy, ethoxy, propyloxy, tert-butoxy, and the like. An "ether" is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl,

—O-aralkyl, —O— heteroaralkyl, —O-carbocylic aliphatic, or —O-heterocyclic aliphatic.

The term "aralkyl", as used herein, refers to an alkyl group substituted with an aryl group.

The term "aryl ring" refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term "aryl" also includes bicyclic ring systems wherein only one of the rings is aromatic, for example, the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

The term "cycloalkyl ring" refers to a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 4 to about 10 carbon atoms, preferably from 4 to 7 carbon atoms, and most preferably from 5 to 6 carbon atoms in the ring. Bicyclic cycloalkyl rings contain from 8 to 12 carbon atoms, preferably from 9 to 10 carbon atoms in the ring. Cycloalkyl rings may be unsubstituted or substituted with from 1 to 4 substituents on the ring. Preferred cycloalkyl ring substituents include halo, cyano, alkyl, heteroalkyl, haloalkyl, phenyl, phenoxy or any combination thereof. More preferred substituents include halo and haloalkyl. Preferred cycloalkyl rings include cyclopentyl, cyclohexyl, cyclohexenyl, cycloheptyl, and cyclooctyl. More preferred cycloalkyl rings include cyclohexyl, cycloheptyl, and cyclooctyl.

The term "carbonyl" is art-recognized and includes such moieties as can be represented by the general formula:

wherein X is a bond or represents an oxygen or a sulfur, and $R_{11}$ represents a hydrogen, hydrocarbon substituent, or a pharmaceutically acceptable salt, R11' represents a hydrogen or hydrocarbon substituent. Where X is an oxygen and $R_{11}$ or $R_{11}'$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R_{11}'$ is hydrogen, the formula represents a "formate". In general, where the oxygen atom of the above formula is replaced by sulfur, the formula represents a "thiocarbonyl" group. Where X is a sulfur and $R_{11}$ or $R_{11}'$ is not hydrogen, the formula represents a "thioester". Where X is a sulfur and $R_{11}$ is hydrogen, the formula represents a "thiocarboxylic acid". Where X is a sulfur and $R_{11}'$ is hydrogen, the formula represents a "thioformate". On the other hand, where X is a bond, $R_{11}$ is not hydrogen, and the carbonyl is bound to a hydrocarbon, the above formula represents a "ketone" group. Where X is a bond, $R_{11}$ is hydrogen, and the carbonyl is bound to a hydrocarbon, the above formula represents an "aldehyde" or "formyl" group.

The term "$C_i$ alkyl" is an alkyl chain having i member atoms. For example, $C_4$ alkyls contain four carbon member atoms. $C_4$ alkyls may be saturated or unsaturated with one or two double bonds (cis or trans) or one triple bond. Preferred $C_4$ alkyls are saturated. Preferred unsaturated $C_4$ alkyls have one double bond. $C_4$ alkyl may be unsubstituted or substituted with one or two substituents. Preferred substituents include lower alkyl, lower heteroalkyl, cyano, halo, and haloalkyl.

The term "halogen" refers to fluoro, chloro, bromo, or iodo substituents. Preferred halogens are fluoro, chloro, and bromo, and more preferred are chloro and fluoro.

The term "heteroalkyl" is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl chains have one or two branches, preferably one branch. Preferred heteroalkyl chains are saturated. Unsaturated heteroalkyl chains have one or more double bonds and/or one or more triple bonds. Preferred unsaturated heteroalkyl chains have one or two double bonds or one triple bond, more preferably one double bond. Heteroalkyl chains may be unsubstituted or substituted with from 1 to about 4 substituents unless otherwise specified. Preferred heteroalkyl chains are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), and amino (e.g., amino, mono- and di-$C_1$-$C_3$ alkylamino, methylphenylamino, methylbenzylamino, $C_1$-$C_3$ alkylamido, carbamamido, ureido, guanidino).

The term "heteroatom" refers to a multivalent non-carbon atom, such as a boron, phosphorous, silicon, nitrogen, sulfur, or oxygen atom, and is preferably nitrogen, sulfur, or oxygen atom. Groups containing more than one heteroatom may contain different heteroatoms.

The term "heteroaryl ring" refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term "heteroaryl" also includes bicyclic ring systems wherein only one of the rings is aromatic, for example, the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

The term "heterocyclic aliphatic ring" is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy, or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl, and piperidyl. Heterocycles can also be polycycles.

The term "hydroxyl" means —OH.

The term "lower alkyl" refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

The term "lower heteroalkyl" refers to a heteroalkyl chain comprised of 1 to 4, preferably 1 to 3 member atoms, more preferably 1 to 2 member atoms. Lower heteroalkyls contain one or two non-adjacent heteroatom member atoms. Preferred lower heteroalkyls contain one heteroatom member atom. Lower heteroalkyls may be saturated or unsaturated. Preferred lower heteroalkyls are saturated. Lower heteroalkyls may be unsubstituted or substituted with one or about two substituents. Preferred substituents on lower heteroalkyl include cyano, halo, trifluoromethyl, and hydroxyl.

The term "$M_i$ heteroalkyl" is a heteroalkyl chain having i member atoms. For example, $M_4$ heteroalkyls contain one or two non-adjacent heteroatom member atoms. $M_4$ heteroalkyls containing 1 heteroatom member atom may be saturated or unsaturated with one double bond (cis or trans) or one triple bond. Preferred $M_4$ heteroalkyl containing 2 heteroatom member atoms are saturated. Preferred unsaturated $M_4$ heteroalkyl have one double bond. $M_4$ heteroalkyl may be unsubstituted or substituted with one or two substituents. Preferred substituents include lower alkyl, lower heteroalkyl, cyano, halo, and haloalkyl.

The term "member atom" refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term "nitro" means —NO$_2$.

The term "pharmaceutically acceptable salt" refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

The term "phenyl" is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy, or any combination thereof. More preferred substituents on the phenyl ring include halo and haloalkyl. The most preferred substituent is halo.

The terms "polycyclyl" and "polycyclic group" refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed "bridged" rings, and rings that are joined through adjacent atoms are "fused rings".

The term "sulfate" is art-recognized and includes a moiety that can be represented by the general formula:

in which R$_{10}$ is as defined above.

A "substitution" or "substituent" on a small organic molecule generally refers to a position on a multivalent atom bound to a moiety other than hydrogen, for example, a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl, or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, for example, which does not spontaneously undergo transformation such as by rearrangement, cyclization, elimination, hydrolysis, etc.

As used herein, the definition of each expression, for example, alkyl, m, n, etc., when it occurs more than once in any structure, is intended to be independent of its definition elsewhere in the same structure.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

In certain embodiments, the subject method employs a fluorescent dye having a structure of the formula:

wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl, for example, optionally substituted by sulfate, phosphate, sulfonate, phosphonate, halogen, hydroxyl, amino, cyano, nitro, carboxylic acid, amide, etc., or a pharmaceutically acceptable salt thereof;

$R_3$ represents, independently for each occurrence, one or more substituents to the ring to which it is attached, such as a fused ring (e.g., a benzo ring), sulfate, phosphate, sulfonate, phosphonate, halogen, lower alkyl, hydroxyl, amino, cyano, nitro, carboxylic acid, amide, etc., or a pharmaceutically acceptable salt thereof;

$R_4$ represents H, halogen, or a substituted or unsubstituted ether or thioether of phenol or thiophenol; and $R_5$ represents, independently for each occurrence, substituted or unsubstituted lower alkyl, cycloalkyl, cycloalkylalkyl, aryl, or aralkyl, for example, optionally substituted by sulfate, phosphate, sulfonate, phosphonate, halogen, hydroxyl, amino, cyano, nitro, carboxylic acid, amide, etc., or a pharmaceutically acceptable salt thereof.

Dyes representative of this formula include indocyanine green, as well as:

In certain embodiments wherein two occurrences of R taken together form a ring, the ring is six-membered, for example, the fluorescent dye has a structure of formula:

wherein X, $R_1$, $R_2$, $R_3$, $R_4$, and $R_5$ represent substituents as described above.

Dyes representative of this formula include IRDye78, IRDye80, IRDye38, IRDye40, IRDye41, IRDye700, IRDye800, Cy7 (AP Biotech), and compounds formed by conjugating a second molecule to any such dye, for example, a protein or nucleic acid conjugated to IRDye800, IRDye40, Cy7, etc. The IRDyes are commercially available from Li-Cor Biosciences of Lincoln, Nebr. It will be appreciated that other dyes may also be used, including the far-red dyes noted above, provided suitable adjustments are made to the visible light imaging components of the imaging system that is used, and other near-infrared dyes or infrared substances, such as quantum dots.

More specifically, IRDye78-CA may be used for imaging the nutrient flow system of a plant. The dye in its small molecule form is generally soluble in the nutrient, and has an in vivo early half-life of several minutes. This permits multiple injections during a single procedure. Indocyanine green has similar characteristics, but is somewhat less soluble in and has a shorter half-life. IRDye78 may also be used in other imaging applications since it can be conjugated to specific ligands. As another example, IR-786, which has been successfully applied, for example, to image blood flow in the heart of a living laboratory rat after a thoracotomy, may also be used to image nutrient flow in a plant, and, more generally, for non-radioactive imaging of target plant portions.

While a number of suitable dyes have been described, it should be appreciated that such fluorescent dyes are examples only, and that more generally, any fluorescent substance may be used with the imaging systems described herein, provided the substance has an emission wavelength that does not interfere with visible light imaging. This includes the fluorescent dyes described above, as well as substances such as quantum dots which may have emission wavelengths above 1000 nm, and may be associated with an antibody, antibody fragment, or ligand and imaged in vivo. All such substances are referred to herein as fluorescent imaging agents, and it will be understood that suitable modifications may be made to components of the imaging system for use with any such fluorescent substance.

Figure 1A:
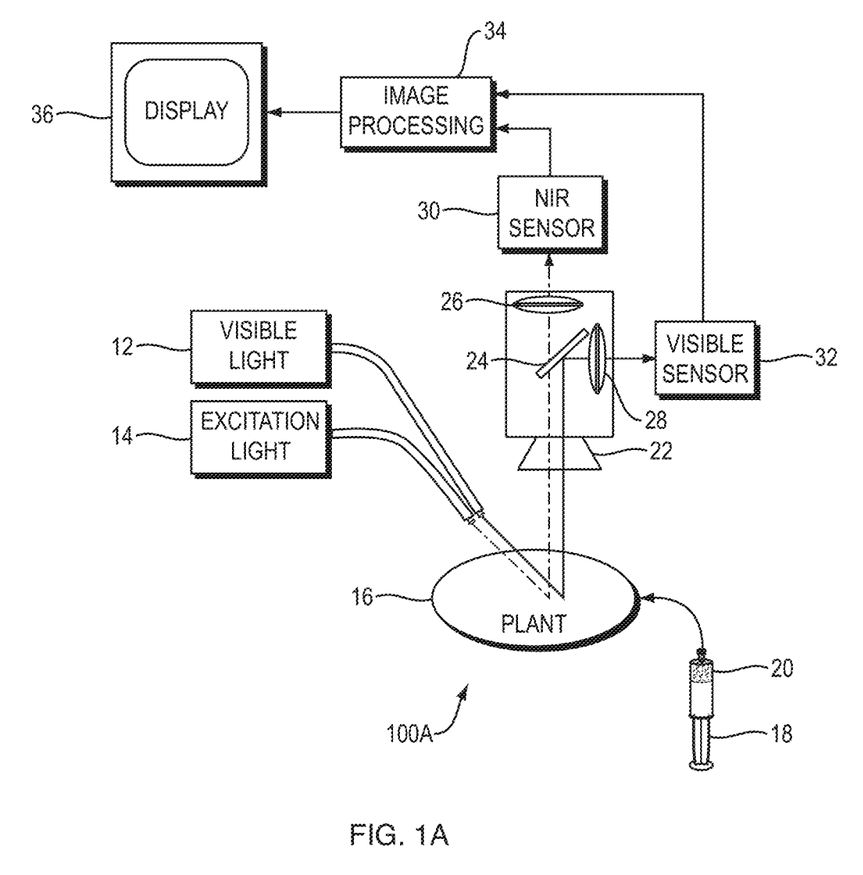
FIGS. 1A-1B show embodiments of a method of imaging a portion of a plant that has absorbed a fluorescent imaging agent is described.

FIG. 1A relates to an embodiment of the present method of using an imaging system 100A to image target portions of a plant 16 that have absorbed a fluorescent imaging agent. The imaging system 100A may include a visible light source 12 (which, in some embodiments, is optional) and an excitation light source 14 (such as a NIR light source) illuminating plant 16 that has absorbed dye (e.g., a fluorescent imaging agent) 20 from dye source 18. Imaging system 100A may further comprise lens 22, first filter 24, second filter 26, third filter 28, near-infrared sensor 30, visible light sensor 32 (which, in some embodiments, is also optional), image processing unit 34 (such as a controller), and display 36. In general, excitation light source 14 may illuminate plant 16 containing dye 20, which may be introduced from dye source 18, such as through injection or absorption into the nutrient flow system of the plant 16. An image from plant 16 may then be captured by near-infrared sensor 30 capturing a fluorescent image based upon the distribution of dye 20 in plant 16. In some embodiments, visible light source 12 may also illuminate the plant with visible sensor 32, capturing a conventional, visible light image of plant 16. The near-infrared sensor 30 and the visible light sensor 32 may capture images simultaneously. Generally, the near-infrared sensor 30 and the visible light sensor 32 can comprise cameras that are capable of capturing visible light, near-infrared light, etc. images. These images may be combined by image processing unit 34 and presented on display 36 where they may be used, for example, by a plant specialist to determine the extent of nutrient flow in the plant 16 or whether the plant 16 has a disease or injury. The plant 16 may be grown in any suitable system, such as an industrial agricultural system, a hydroponic system, etc.

Figure 1B:
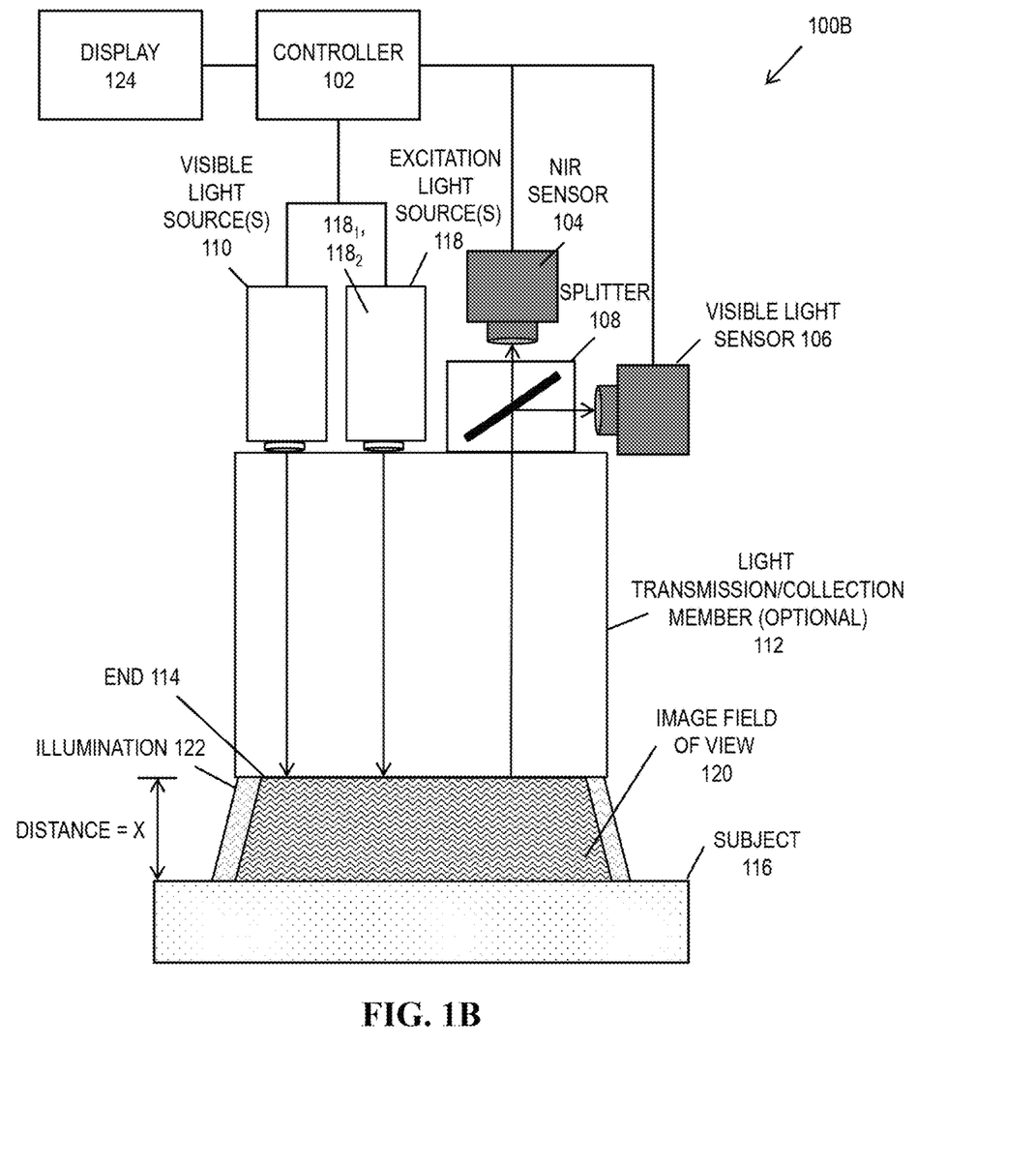

FIG. 1B shows an embodiment of an imaging system 100B that may be used, for example, to image a portion of a plant 16 either in vivo or ex vivo. The imaging system 100B may generally include a controller 102, a display 124, a near-infrared (NIR) sensor 104, one or more excitation light source(s) 118, a visible light sensor 106, a splitter mechanism 108, one or more visible light source(s) 110, and/or a light transmission/collection member 112. As would be appreciated, imaging system 100B may be adapted for any number of uses including, but not limited to, open surgical imaging, endoscopic or laparoscopic imaging, block face imaging (e.g., of a tissue sample), or the like. Examples of imaging system 100B include the FLARE® (FLuorescence-Assisted Resection and Exploration) imaging systems available from Curadel LLC, Marlborough, Mass., as well as any other type of optical imaging system.

In various embodiments, imaging system 100B may be configured to capture fluorescence images of a subject 116, such as a portion of a plant, using the near-infrared (NIR) sensor 104 and the visible light sensor 106. Prior to imaging subject 116 and/or during the imaging by imaging system 100B, subject 116 may be injected with or absorb a fluorescent dye (e.g., a fluorophore) that is optically reactive when exposed to certain wavelengths of light. Generally, subject 116 may be any form of organic tissue (e.g., trunk of a plant) in an open or laparoscopic/endoscopic setting, in various embodiments. For example, some dyes may be photo-reactive to certain wavelengths and emit light in the NIR range when exposed to illumination in this range. Leveraging this, imaging system 100B may capture contrasting images of subject 116 with NIR sensor 104 capturing the phosphorescence/NIR images of subject 116 and the dye infused therein, and visible light sensor 106 capturing visible light images of subject 116. In general, near-infrared as used herein refers to the range of wavelengths between 660-900 nanometers ("nm").

Generally, and as described in more detail below, controller 102 may provide electronic control over visible light source(s) 110, one or more excitation light source(s) 118, NIR sensor 104 and visible light sensor 106, to capture the NIR and visible light images of subject 116, respectively. Controller 102 may also, in some embodiments, combine the imaging data from both types of captured images into a combined image. For example, such a combined image may present the NIR/fluorescence image data as an overlay for the visible image data, thereby providing a visual indication of the locations within subject 116 where the fluorescent dye is located. For example, certain dyes may bind to specific tissues of a plant 16, thereby facilitating visualization of the tissues within subject 116. In another example, such a dye may be injected into the nutrient flow of a plant 16, thereby allowing the user of imaging system 100B to visualize the nutrient flow within subject 116. Once the NIR and visible light image data has been processed, controller 102 may provide the processed image data to a local or remote (e.g., connected via a network) display 124 for visualization and review by a user.

In some embodiments, visible light source(s) 110 may include a visible light source that serves as a light source for visible light sensor 106. For example, the visible light source may be, for example, a near-infrared depleted white light source that provides illumination 122 to subject 116. Notably, this may be a one-hundred and fifty Watt halogen lamp with one or more filters to deplete wavelengths greater than 700 nm. Generally, any light source constrained to wavelengths between 400 nm and 700 nm may operate as the visible light source in the visible light source(s) 110. In further embodiments, however, ambient lighting in the area may be used in part, or in whole, to provide the visible illumination to subject 116.

In some cases, imaging system 100B may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose an image field of view 120, light source(s) 110, 118 and sensors 104, 106 in an area that is not exposed to broadband light sources. This may be achieved by using an operating room closed to external light sources, or by using a hood or other enclosure or covering for the image field that prevents invasion by unwanted spectrum. In other cases, this can be achieved simply by lowering the interfering light sources to a level where the imaging system 100B in minimally affected. The visible light source(s) 110 may then serve as a light source for the visible light sensor 106, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a plant, and do not include an operating area as that term is intended herein.

In addition to capturing visible light images of subject 116, NIR sensor 104 of imaging system 100B may capture NIR images of subject 116 (and the fluorescent dye present therein) as illuminated by an excitation light source 118 (e.g., by providing excitation illumination 122 to subject 116). For example, in certain applications, the excitation light source 118 and resulting emission from the dye present in subject 116 may have wavelengths near or below 700 nm, as with Cy5 dye, which emits light when excited at 650 nm. These near-red dyes may be used with the present system. However, this requires a visible light source 110 that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source 110 should be depleted at the wavelength(s) of interest. As such, the visible light source 110 should more generally be understood to be a source of light that includes some, but not necessarily all, of the wavelengths of visible light.

It should also be understood that, in a far-red imaging system or infrared imaging system such as those noted above, NIR sensor 104 described in the example embodiment will instead be a sensor sensitive to the emission wavelength of the injected dye or other fluorescent substance, and that other modifications to light sources, filters and other optics will be appropriate. Similar modifications may be made to isolate a band of wavelengths for dye excitation and emission anywhere within or outside the visible light range, provided that suitable optics, sensors, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source and the emission sensor, the NIR sensor in the example embodiment, for such applications. Sensors sensitive to far-red, near-infrared, and infrared wavelengths are commercially available.

In particular, excitation light source 118 may provide light at a wavelength that excites the dye present in subject 116. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by visible light sensor 106 (e.g., a video camera, etc.) or the emission wavelength of the dye. The near-infrared band is generally understood to include wavelengths between 700 nm and 1000 nm, and is a useful wavelength range for a number of readily available excitation light sources and dyes that may be used with the systems described herein. Suitable optical coupling and lenses may be provided to direct each of the visible light source and the excitation light source at an area of interest of subject 116.

Generally, splitter 108 may be operable to separate and direct the NIR and visible light received from the illuminated subject 116. For example, splitter 108 may include any number of filters and/or dichroic mirrors, to direct the fluorescence wavelengths towards NIR sensor 104 and the visible wavelengths towards visible light sensor 106 for capture. A number of arrangements of the sensors 104, 106 and splitter 108 are possible, and may involving reflecting or transmitting either the visible light image or the emission wavelength image.

In various embodiments, imaging system 100B may also include a light transmission/collection member 112 that conveys the light from light source(s) 110, 118 to the surface subject 116 and direct any light (e.g., reflected light, etc.) from subject 116 towards splitter 108 and sensors 104, 106. For example, light transmission/collection member 112 may include any number of fiber optics or other light guides/channels, to direct the illumination from light source(s) 110, 118 towards subject 116 and the captured light from subject 116 towards sensors 104, 106. In further embodiments, light source(s) 110 may be decoupled from light transmission/collection member 112, to provide illumination to subject 116 directly. In some embodiments, light transmission/collection member 112 may also include any number of lenses on its distal end 114, to transmit light from light source(s) 110, 118 towards subject 116 and collect light from subject 116 for processing by sensors 104, 106.

Typically, the light provided by visible light source(s) 110 and from excitation light source(s) 118 may be transmitted via different channels within light transmission/collection member 112. In other embodiments, they may be mixed. Note, also, that light transmission/collection member 112 may be optional, in some embodiments. For example, while endoscopic, laparoscopic, etc. application may employ member 112, other implementations, such as open surgical procedures, may not require member 112 and this component can be omitted.

NIR sensor 104 may be any form of sensor capable of capturing still images or moving images in the NIR portion of the spectrum. Notably, in some embodiments, NIR sensor 104 may be a still or moving image camera suitable for capturing images at the emission wavelength of the excited dye present in subject 116. The near-infrared camera may be, for example, an Orca-ER near-infrared camera with settings of gain 7, 2×2 binning, 640×480 pixel field of view, and an exposure time of 20 ms and an effective frame rate of fifteen frames per second. The Orca-ER is commercially available from Hamamatsu Photonic Systems of Bridgewater, N.J. It will be understood that the NIR sensor 104 in FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term "emission wavelength camera" is intended to refer to any such camera that may be used with the systems described herein.

Visible light sensor 106 may be any form of sensor capable of capturing still images or video of subject 116 in the visible portion of the spectrum. In one embodiment, visible light sensor 106 may be a video camera suitable for capturing images of subject 116 in the visible light spectrum. In further embodiments, visible light sensor 106 may instead be a camera configured to take still images, as opposed to video. In one embodiment, sensor 106 is a color video camera model HV-D27, commercially available from Hitachi of Tarrytown, N.Y. For example, the video camera 106 may capture red-green-blue (RGB) images at thirty frames per second at a resolution of 640×480 pixels, or at any other number of frames or resolutions, as desired. In another example, sensor 106 may be a high resolution Canon EOS 700 white light camera available from Canon, Melville, N.Y., although any other suitable white light camera can be used in other implementations. More generally, NIR sensor 104 and visible light sensor 106 may be any device capable of photonic detection and conversion to electronic images, including linear photodiode arrays, charge coupled device arrays, scanning photomultiplier tubes, and so forth.

As would be appreciated, NIR sensor 104 and visible light sensor 106 may be implemented in any number of ways. For example, in some cases, NIR sensor 104 and visible light sensor 106 may be implemented as separate cameras coupled to splitter 108. In other cases, however, NIR sensor 104 and visible light sensor 106 may be implemented as a single, multi-spectral camera capable of capturing both visible light and NIR images.

Display 124 may be a television, high-definition television, computer monitor, or other display configured to receive and render signals from controller 102. In some embodiments, display 124 may be a monocular or binocular eyepiece of the surgical microscope, with the near-infrared image superimposed on the visible light image in the eyepiece. In another embodiment, the eyepiece may use direct optical coupling of the surgical field to the eyepiece for conventional microscopic viewing, with the near-infrared image projected onto the eyepiece using, for example, heads-up display technology.

Generally, the controller 102 should be capable of digital filtering, gain adjustment, color balancing, and/or any other image processing functions. The image from the NIR sensor 104 is also typically shifted into the visible light range for display at some prominent wavelength, e.g., a color distinct from the visible light colors of the captured and/or displayed image data from sensor 106, so that a superimposed image will clearly depict the dye. The controller 102 may also perform image processing to combine the image from the NIR sensor 104 and the visible light sensor 106. Where the images are displayed side-by-side, this may simply entail rendering the images in suitable locations on a computer screen. Where the images are superimposed, a frame rate adjustment may be required. That is, if the visible light sensor 106 is capturing images at the conventional rate of thirty frames per second and the NIR sensor 104 is taking still pictures with an effective frame rate of fifteen frames per second, some additional processing may be required to render the superimposed images concurrently. This may entail either reducing the frame rate of the visible light sensor 106 to the frame rate of the NIR sensor 104 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

In one embodiment, the visible light source of light source(s) 110 is a near-infrared depleted visible light source, the excitation light source 118 is a 760 nm, 2.5 W laser diode, the dye is indocyanine green or ZW800-1, and imaging system 100B includes a 780 nm dichroic mirror (e.g., splitter 108) configured to transmit near-infrared light and reflect visible light, the a 781 nm longpass emission filter, and a 400 nm to 700 nm filter. The controller 102 comprises a processing circuit configured with software for image capture from the NIR sensor 104 and the visible light sensor 106, for making suitable color adjustment to the images from the NIR sensor 104, for making frame rate adjustments to the visible light sensor 106 image, and for combining the two images for superimposed display on the display 124.

In further embodiments, imaging system 100B may be adapted for use in an endoscope or laparoscope. Typically, a laparoscope is inserted into a body cavity through an incision, as distinguished from an endo scope that is inserted through an existing opening of a plant. A laparoscope has a different form factor than an endoscope, including different dimensional requirements. It will further be appreciated that the imaging system 100B may be used to simplify imaging devices other than endoscopes and laparoscopes, such as by providing an integrated, coaxial illumination and image capture device using the techniques described above.

In some embodiments, imaging system 100B may be configured to capture NIR images at different wavelengths, using any number of channels. For example, excitation light source(s) 118 may include lasers (e.g., laser diodes or other emitters) that illuminate the subject with light at different wavelengths. This may be done in an alternating or staggered manner, so as to capture the images under the different NIR illumination conditions via NIR sensor 104. Table 1 below shows an example of such a dual NIR illumination setup:

TABLE 1

| Type | Illumination | Light Collection |
|---|---|---|
| Color Video | 400-650 nm | 400-650 nm |
| NIR Channel 1 (NIR 1) | 665 ± 2 nm laser | 685-735 nm |
| NIR Channel 2 (NIR 2) | 760 ± 2 nm laser | ≥781 nm |

Figure 2A:
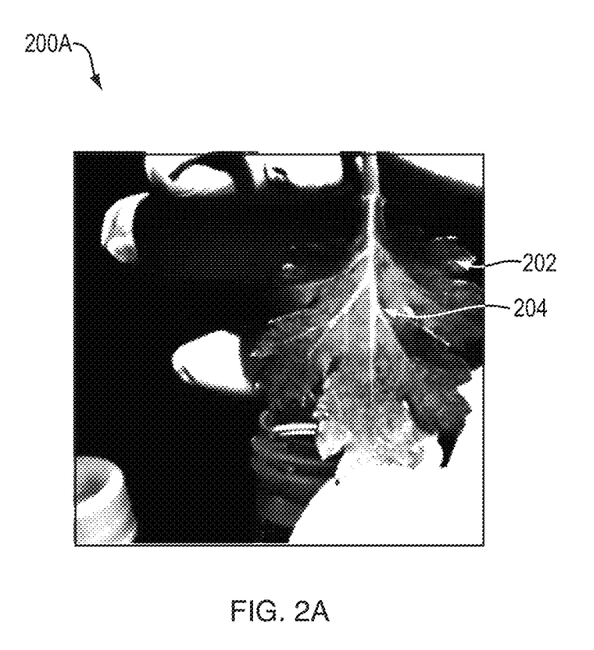
FIGS. 2A-2B show examples of displayed images from illuminating portions of a plant.
Figure 2B:
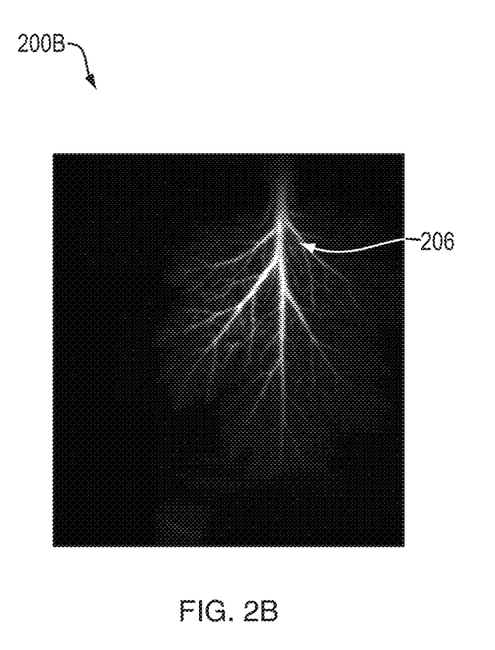

FIGS. 2A-B each show example images resulting from the method described herein. In particular, FIG. 2A shows an example 200A of illuminating of a plant leaf 202 of a plant into which a fluorescent dye (e.g., a fluorescent imaging agent) has been absorbed by the plant. As shown, the light source, comprising both a visible light source and a NIR light source, illuminates the leaf 202 and causes fluorescent emission 204 from the dye (visible as white regions within the leaf nutrient flow system). Turning to FIG. 2B, FIG. 2B shows a displayed image 200B resulting from superimposition of a visible light image and a NIR light image. As shown in FIG. 2B, the displayed image 200B comprises the fluorescent emission 206 from the dye (visible as white regions).

Figure 3:
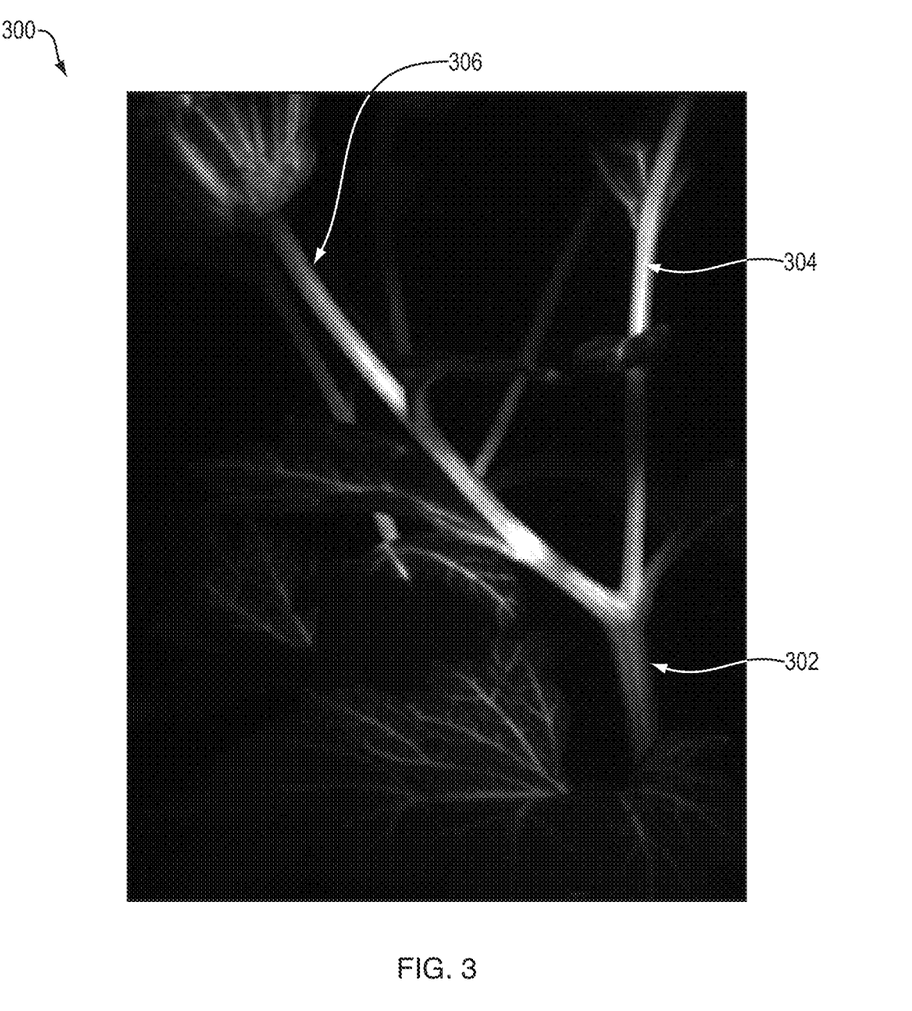
FIG. 3 shows another example of a displayed image from illuminating portions of a plant.

With reference to FIG. 3, FIG. 3 shows a displayed superimposed image 300 resulting from illumination of the stem 302 and branch portions 304-306 of a plant that include a fluorescent imaging agent, using the method described herein. As can be seen, the nutrient flow system of the plant is clearly visible, along with portions of the plant itself, enabling determination and measurement of nutrient flow, such as the width of the xylem pathway, rate of flow (speed), etc. In this way, the flow of nutrients through the plant can be assessed and monitored in real time, without damage to the plant, and constrictions or other regions of reduced nutrient flow can be identified and, if necessary, removed or otherwise addressed. Healthy portions of the plant can be readily determined, as well as regions in which the health of the plant has been compromised. Additionally, a determination as to whether the plant has a disease or injury based on, for example, the superimposed image 300 can be made.

In an example, the superimposed image 300 can be assessed using a machine learning process to identify an obstruction in the nutrient flow, the disease, or the injury of the stem 302 and/or the branch portions 304-306. The superimposed image 300 can be assessed to determine a percentage or speed of the nutrient flow of the shown portions of the plant.

Furthermore, two (or more) fluorescent dyes may be introduced to and absorbed by the plant, where each dye of the two fluorescent dyes can be caused to release different fluorescent emissions when excited by two different NIR light sources $118_1$ $118_2$ (FIG. 1B) with different wavelengths (that correspond to each of the two fluorescent dyes in accordance with what has been previously described). Using the two fluorescent dyes may facilitate an assessment of two separate locations, tissues, etc. of the plant. For example, a 700 nm tracer fluorescent dye can be initially introduced to and absorbed in the roots of a plant, where a flow rate can be measured as the tracer fluorescent dye travels up to the leaves from the roots. Then an intervention can be performed, for example, treating the plant with an insecticide, prior to introducing an additional tracer fluorescent dye that is absorbed by the plant. Subsequent to introducing the additional tracer fluorescent dye, an additional flow rate can be measured as the additional tracer fluorescent dye travels up to the leaves from the roots and a comparison can be made to determine, for example, the effectiveness of the intervention (e.g., insecticide).

Said differently, an additional NIR light source $118_2$ may be implement that illuminates a portion of the plant to cause additional fluorescent emission by an additional florescent imaging agent simultaneously with the NIR light source $118_1$. The imaging system 100B may then receive the additional fluorescent emission from the illuminated portion of the plant and generate an additional florescent image of the portion of the plant from the received visible light emission. The resulting fluorescent image is then superimposed on the additional fluorescent image and displayed on the imaging system.

In another example, dual imaging by way of two (or more) fluorescent dyes can permit independent measurement of flow from the "roots up" (using one NIR wavelength) and from the "stoma in" (using a different NIR wavelength), in accordance with the techniques described herein. Additionally, two independent wavelengths (corresponding to two fluorescent dyes) permit RATIOMETRIC imaging using dyes that sense pH, redox potential, voltage potential, etc. Further, environmental-sensing dyes typically shift wavelength in response to the parameter being measured, and, because the present invention has two independent emission channels, the ratio of these two channels provides either relative (if not calibrated) or absolute (if calibrated using a standard curve) measurement of parameters corresponding to a dye (e.g., pH, redox status, etc.).

Thus, as described above, a visible light image may be captured of target portions of a plant. The visible light image may include a subset of visible light wavelengths when an optical channel for dye imaging includes a wavelength within the visible light range. A near-infrared image may also captured of the same (or an overlapping) field of view of the target portion of the plant. Although referred to here for convenience as a near-infrared image, it should be clear that the dye-based image may also, or instead, employ other wavelengths, such as far-red or infrared wavelengths. The near-infrared image may be shifted to a visible wavelength for display, preferably using a color that is prominent when superimposed on the visible light tissue image. The images may be frame-rate adjusted as appropriate for video display of the surgical field. Either image may also be displayed separately if desired for flow analysis and monitoring.

Figure 4:
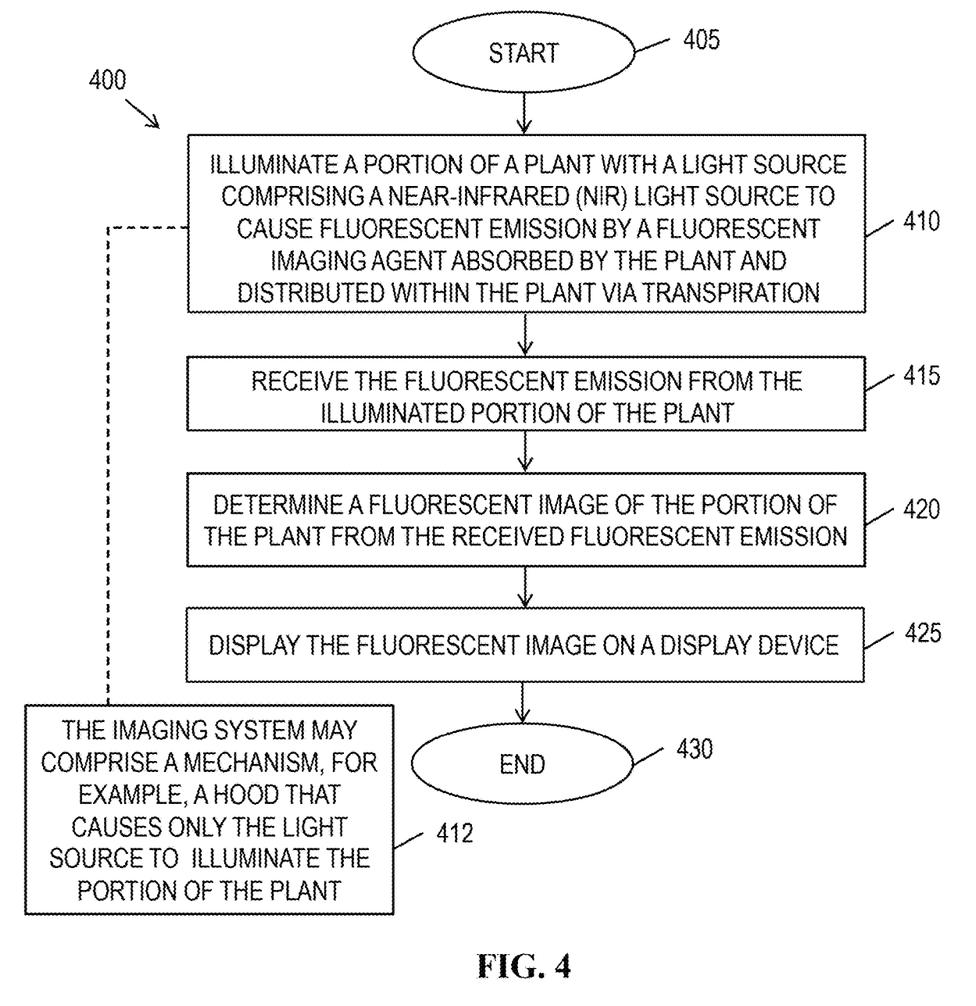
FIG. 4 shows an example simplified procedure for imaging a portion of a plant that has absorbed a fluorescent imaging agent.

FIG. 4 illustrates an example simplified procedure in accordance with the embodiments herein. In general, procedure 400 may be performed by an imaging system having a processing circuit that executes stored machine instructions. Procedure 400 may start at step 405 and continues on to step 410 where, as described in greater detail above, the imaging system illuminates a portion of a plant with a light source comprising a near-infrared (NIR) light source to cause fluorescent emission by a fluorescent imaging agent absorbed by the plant and distributed within the plant via transpiration. The fluorescent imaging agent may be a dye that can be introduced as a solution in the nutrient to be transported through the plant. The fluorescent dye may be supplied to the plant in a nutrient and water-based solution either intermittently or continuously. The plant can absorb the fluorescent imaging agent via roots (through transpiration) or stomata. For example, the fluorescent imaging agent can comprise IRDye78-CA. In some embodiments, the NIR light source provides light at a wavelength that causes the imaging agent to fluoresce, while the visible light source provides light that is near-infrared depleted, particularly at the excitation wavelength of the imaging agent. Further, as shown by step 412, the imaging system may comprise a mechanism, for example, a hood that causes only the light source to illuminate the portion of the plant.

In step 415, as described in greater detail above, the imaging system receives the fluorescent emission from the illuminated portion of the plant. In embodiments where the light source additionally comprises the visible light source, the imaging system may additionally receive visible light emission from the illuminate portion of the plant.

In step 420, as described in greater detail above, the imaging system generates a fluorescent image of the portion of the plant from the received fluorescent emission. The imaging system may include both a visible light sensor, configured to capture visible light images from the illuminate portion, and further includes a NIR light sensor capturing the NIR images from the illuminated portion. The sensors may receive light from the same surface illuminated by the light source. For example, the light source and the sensors may both be positioned above the target portion of the plant, with the sensors receiving light reflected or emitted by the plant. Further, the NIR light sensor and the visible light sensor can be configured to simultaneously capture the images, in some embodiments.

In step 425, the imaging system displays, on a display device of the imaging system, the fluorescent image. For example, as described in greater detail above, the imaging system may include a controller configured to covert the received light into separate visible images and NIR images. The controller can be configured to superimpose the visible and NIR images, when outputting the display data for display. Based on the fluorescent image, a determination that the plant has a disease or injury can be made, either automatically by the imaging system or another device in communication therewith or, in further cases, by the end user reviewing the displayed image. In particular, an obstruction in a nutrient flow of the plant can be identified, a percentage of the nutrient flow can be determined, or a speed of the nutrient flow and be determined. Alternatively, a machine learning process can be performed by, for example, a computing system, to identify the disease or injury directly from the captured image data (e.g., by applying an image classifier to the image, etc.). Procedure 400 then ends at step 430.

It should be noted that while certain steps within procedure 400 may be optional as described above, the steps shown in FIG. 4 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

It will be appreciated that the above functionality is merely illustrative, and that other dyes, imaging hardware, and optics may be usefully deployed with the imaging systems described herein. For example, any of the imaging systems may be used as described above with excitation and/or emission wavelengths in the far-red spectrum. Through minor adaptations that would be clear to one of ordinary skill in the art, the system could be configured to image two or more functions at the same time that a visible light image is captured by associating each function with a different dye having a different emission wavelength. These and other arrangements and adaptations of the subject matter discussed herein are intended to fall within the scope of the invention.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to medical and research imaging, the techniques herein are not limited as such and can be adapted for use in other industries, as well.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method, comprising:
illuminating, by an imaging system, a portion of a plant with a light source comprising a near-infrared (NIR) light source to cause fluorescent emission by a fluorescent imaging agent absorbed by the plant and distributed within the plant via transpiration;
receiving, by the imaging system, the fluorescent emission from the illuminated portion of the plant;
generating, by the imaging system, a fluorescent image of the portion of the plant from the received fluorescent emission; and
displaying, on a display device of the imaging system, the fluorescent image.

2. The method of claim 1, further comprising:
determining that the plant has a disease or an injury based on the fluorescent image.

3. The method of claim 2, wherein determining that the plant has the disease or the injury based on the fluorescent image comprises identifying an obstruction in a nutrient flow of the plant based on the fluorescent image.

4. The method of claim 2, wherein determining that the plant has the disease or the injury based on the fluorescent image comprises determining that a percentage of a nutrient flow of the plant is not shown in the fluorescent image.

5. The method of claim 2, wherein determining that the plant has the disease or the injury based on the fluorescent image comprises determining a speed of a nutrient flow of the plant based on the fluorescent image.

6. The method of claim 2, wherein determining that the plant has the disease or the injury based on the fluorescent image comprises performing a machine learning process to identify the disease or the injury.

7. The method of claim 1, wherein the fluorescent imaging agent comprises IRDye78-CA.

8. The method of claim 1, wherein the plant absorbs the fluorescent imaging agent via roots of the plant.

9. The method of claim 1, wherein the plant absorbs the fluorescent imaging agent via stomata of the plant.

10. The method of claim 1, further comprising:
allowing, by the imaging system, only the light source to illuminate the portion of the plant.

11. The method of claim 10, wherein allowing, by the imaging system, only the light source to illuminate the portion of the plant comprises using a hood.

12. The method of claim 1, wherein the fluorescent emission is in a wavelength of 660 nanometers (nm) to 900 nm.

13. The method of claim 1, wherein the light source further comprises a visible light source, the method further comprising:
illuminating, by the imaging system, the portion of the plant with the light source to cause visible light emission by the portion of the plant simultaneously with the NIR light source;
receiving, by the imaging system, the visible light emission from the illuminated portion of the plant; and
generating, by the imaging system, a visible light image of the portion of the plant from the received visible light emission.

14. The method of claim 13, wherein displaying, on the display device of the imaging system, the fluorescent image comprises superimposing the fluorescent image on the visible light image.

15. The method of claim 1, wherein displaying, on the display device of the imaging system, the fluorescent image comprises displaying a video of the portion of the plant.

16. The method of claim 1, further comprising providing an interventional treatment to the plant before or after generating the fluorescent image of the portion of the plant.

17. The method of claim 1, wherein the fluorescent image is a first fluorescent image, the method further comprising:
treating the plant with an insecticide; then,
illuminating, by the imaging system, the portion of the plant with the light source comprising the near-infrared (NIR) light source to cause a second fluorescent emission by a second fluorescent imaging agent absorbed by the plant and distributed within the plant via transpiration;
receiving, by the imaging system, the second fluorescent emission from the illuminated portion of the plant;
generating, by the imaging system, a second fluorescent image of the portion of the plant from the received second fluorescent emission; and
comparing the first fluor scent, image and the second fluorescent image to thereby evaluate an effectiveness of the insecticide.

18. The method of claim 1, further comprising, before and/or during the illuminating step, supplying a water solution to the plant, wherein the water solution comprises the fluorescent imaging agent and the fluorescent imaging agent is soluble in the water solution.

19. A method of evaluating a plant, comprising:
supplying a fluorescent imaging agent to a plant in a nutrient and water-based solution;
illuminating, by an imaging system, a portion of the plant with a light source comprising a near-infrared (NIR) light source to cause fluorescent emission by the fluorescent imaging agent absorbed by the plant and distributed within the plant;
receiving, by the imaging system, the fluorescent emission from the illuminated portion of the plant;
generating, by the imaging system, a fluorescent image of the portion of the plant from the received fluorescent emission; and
displaying, on a display device of the imaging system, the fluorescent image.

20. The method of claim 19, wherein supplying the fluorescent imaging agent to the plant in the nutrient and water-based solution comprises intermittently supplying the fluorescent imaging agent.

21. The method of claim 19, wherein supplying the fluorescent imaging agent to the plant in the nutrient and water-based solution comprises continuously supplying the fluorescent imaging agent.

22. A method, comprising:
illuminating, by an imaging system, a portion of a plant with a light source comprising a near-infrared (NIR) light source to cause fluorescent emission by a fluorescent imaging agent absorbed by the plant and distributed within the plant via transpiration;
receiving, by the imaging system, the fluorescent emission from the illuminated portion of the plant;
generating, by the imaging system, a fluorescent image of the portion of the plant from the received fluorescent emission; and
displaying, on a display device of the imaging system, the fluorescent image,
wherein the light source further comprises an additional NIR light source, the method further comprising:
illuminating, by the imaging system, the portion of the plant with the additional NIR light source to cause additional fluorescent emission by an additional florescent imaging agent simultaneously with the NIR light source;
receiving, by the imaging system, the additional fluorescent emission from the illuminated portion of the plant; and
generating, by the imaging system, an additional fluorescent image of the portion of the plant from the received additional fluorescent emission.

23. The method of claim 22, wherein displaying, on the display device of the imaging system, the fluorescent image comprises superimposing the fluorescent image on the additional fluorescent image.

* * * * *

UNITED STATES PATENT AND TRADEMARK OFFICE
CERTIFICATE OF CORRECTION

PATENT NO. : 10,852,236 B2
APPLICATION NO. : 16/127476
DATED : December 1, 2020
INVENTOR(S) : John V. Frangioni It is certified that error appears in the above-identified patent and that said Letters Patent is hereby corrected as shown below:

In the Specification

Column 3, Lines 22-35: Please delete the following structure:

" "

And replace with:

-- --

Column 5, Line 1: Please correct "—O— heteroaralkyl" to read -- —O-heteroaralkyl --

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

Column 10, Lines 30-40: Please delete the following structure:

""

And replace with:

--                                              --

In the Claims

Column 21, Line 21, Claim 17: Please correct "fluor scent, image" to read -- fluorescent image --